United States Patent

Hall et al.

[11] Patent Number: 6,145,372
[45] Date of Patent: Nov. 14, 2000

[54] APPARATUS AND METHOD FOR DETECTING IMPURITIES IN WET CHEMICALS

[75] Inventors: Lindsey H. Hall, Dallas; Jennifer Sees, The Colony; Oliver Chyan, Denton, all of Tex.

[73] Assignee: Texas Instruments Incorporated, Dallas, Tex.

[21] Appl. No.: 09/069,908

[22] Filed: Apr. 30, 1998

Related U.S. Application Data

[60] Provisional application No. 60/045,208, Apr. 30, 1997.
[51] Int. Cl.[7] .......................... G01N 27/403; G01N 33/00
[52] U.S. Cl. .......................................... 73/53.01; 73/61.41
[58] Field of Search ................................ 73/53.01, 61.41, 73/61.42, 61.62

[56] References Cited

U.S. PATENT DOCUMENTS

| | | | |
|---|---|---|---|
| 4,440,620 | 4/1984 | Ono et al. | 204/403 |
| 4,918,812 | 4/1990 | Parce et al. | 204/403 |
| 5,395,503 | 3/1995 | Parce et al. | 204/403 |
| 5,489,515 | 2/1996 | Hatschek et al. | 204/403 |

OTHER PUBLICATIONS

Chyan et al., "A New Potentiometric Sensor for the Detection of Trace Metallic Contaminants in Hydrofluoric Acid", *J. Electrochem. Soc.*, vol. 143, No. 10, Oct. 1996, pp. L235–L237.

*Primary Examiner*—Daniel S. Larkin
*Attorney, Agent, or Firm*—Wade James Brady, III; Frederick J. Telecky, Jr.

[57] ABSTRACT

A apparatus and method for monitoring impurities in wet chemicals in semiconductor wafer processing comprising a silicon sensor (12) that is electrically connected to a potentiometer (22), a reference electrode (14) electrically connected to the potentiometer (22), wherein a comparison in the potential between the silicon sensor (12) and the reference electrode (14) to a predetermined baseline is used to measure wet chemical impurities, is disclosed.

20 Claims, 3 Drawing Sheets

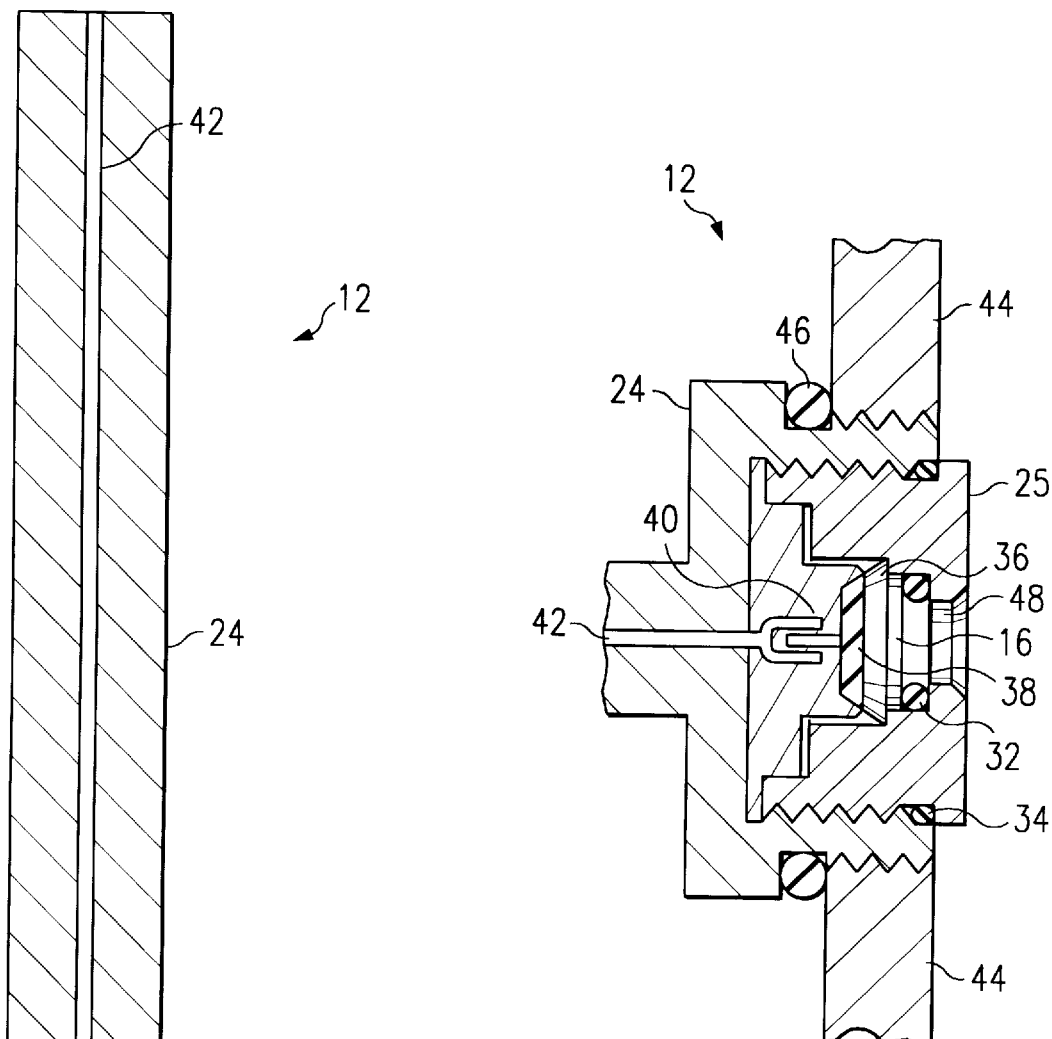
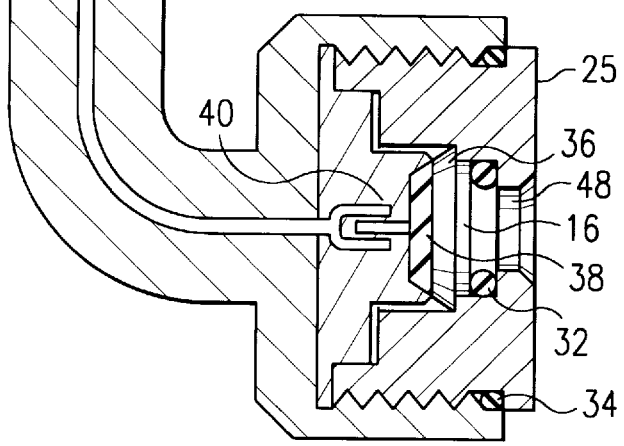
FIG. 2
FIG. 3

APPARATUS AND METHOD FOR DETECTING IMPURITIES IN WET CHEMICALS

This application claims priority under 35 USC § 119(e)(1) of provisional application No. 60/045,208 filed Apr. 30, 1997.

TECHNICAL FIELD OF THE INVENTION

The present invention relates in general to the field of sensors, more particularly the present invention is related to an apparatus and method for using a silicon chip based sensor for detecting impurities during a silicon wafer manufacturing process.

BACKGROUND OF THE INVENTION

Without limiting the scope of the invention, its background is described in connection with the manufacture of silicon wafers, as an example.

Heretofore, in this field, a series of wet chemical washing steps follow the deposition of operative layers on silicon wafers. In the process for fabricating modern semiconductor integrated circuits, it is necessary to form conductive lines or other structures above previously formed structures. It has been found that irregularities on the wafer surface may be caused by impurities in wet chemical washing steps, which lead to irregularities during the deposition of subsequent layers.

The irregularities caused by the outplating of ions, such as metallic or organic ions, can easily result in incomplete coverage, breaks in the deposited material, or voids when a subsequent layer is deposited directly over the aforementioned highly irregular surfaces. Outplating occurs when ions, normally metallic or organic, leach out from a wash solution, such as hydrofluoric acid, and become deposited on a silicon substrate. Even trace levels of outplated impurities can lead to degradation of minority carrier lifetime leading to a premature breakdown of gate oxide layers.

Unfortunately, these irregularities can not be alleviated at the next major processing step, because it is assumed that the top surface topography of the surface is at its cleanest following a washing step. These irregularities will tend to become even more pronounced as subsequent layers are deposited, causing further problems as the layers stack up in the subsequent processing of the semiconductor structure.

Depending upon the types of material used and their intended purposes, numerous undesirable characteristics are produced when these outplating irregularities occur. Incomplete coverage of an insulating oxide layer can lead to short circuits between metalization layers. Likewise, voids may trap air or processing gases, either contaminating further processing steps, creating weak spots in the film or simply lowering overall device reliability. Sharp points on conductors may result in unusual, undesirable field effects and high current densities. One problem that is widely recognized in the wafer manufacturing process is that, in general, processing high density circuits over highly irregular structures can lead to very poor yields and device performance.

Consequently, it is necessary to insure the integrity and purity of the wet chemicals used in the washing steps in order to facilitate the processing of multi-layer integrated circuits and to improve their yield, performance, and reliability. In fact, all of today's high-density integrated circuit fabrication techniques make use of wet chemical washing steps prior to the deposition of new gate oxide structures at critical points in the fabrication process.

Impurities in wet chemicals have been identified by monitoring the yield of silicon chips derived from a silicon wafer. During the fabrication of very large scale integrated circuits, for example, large amounts of wet chemicals are used in the washing steps that accompany the etching and polishing phases of silicon wafer manufacture prior to a high temperature operation.

It has been found that present methods are unable to detect levels of contamination that lead to wash chemical outplating. Current methods of detecting impurities in washing solutions involve the off-line analysis of samples using, for example, plasma-mass spectroscopy. Among the problems associated with using mass-spectroscopy are lag-time between the time the sample is taken and analyzed, and sensitivity. In addition, plasma-mass spectroscopy is not performed on a daily basis due to the extensive cost of the operation and the waste of resources.

As already mentioned, a significant problem of current monitoring techniques is low sensitivity. The sensitivity of current electrochemical sensors is theoretically limited by the Nernst equation to a maximum sensitivity of 59 mV per decade change in ionic concentration.

Therefore, what is needed is a sensing device that is compatible with silicon wafer fabrication sequences. Furthermore, a need has arisen for an in-line wet chemical contamination monitor that detects impurities beyond the range of electrochemical sensors. Also, there is a need for wafer manufacturing techniques and procedures for use in identifying the onset of wet chemical contamination before a large number of defective silicon wafers are produced due to the undetected contamination.

SUMMARY OF THE INVENTION

The present invention solves the problems associated with the monitoring of metallic and organic contamination of wet chemicals used in the manufacture of silicon wafers. To address these problems an apparatus and method is disclosed for detecting impurities in wet chemicals used in semiconductor wafer processing comprising a silicon sensor that is electrically connected to a potentiometer to detect impurities in the wet chemicals used in semiconductor wafer processing. A reference electrode, also electrically connected to the potentiometer, is used to obtain an open circuit potential between the silicon sensor and the reference electrode. Further, a recording device may be connected to the potentiometer, such as a computer, printer, or an alarm.

In one embodiment of the present invention, the reference electrode used to compare the output of the silicon sensor is a solid state reference electrode. Alternatively, a quasi solid state reference electrode, or a double-junction electrode may be used. Also, a Ag/AgCl based double-junction reference electrode may be used with the present invention.

A type of potentiometer that may be used with the present invention is a pH meter. The silicon sensor of the present invention includes a silicon chip that is in its native state. In one embodiment, the silicon chip has an operative side that is polished. The operative side of the silicon chip is exposed to the semiconductor wafer processing wet chemicals. In one alternative embodiment, the operative side of the silicon chip may have an oxide layer disposed thereon. The silicon chip used in the silicon sensor may be a n-Si arsenic-doped chip, but may also be p-type or polysilicon. Alternatively, the selection of a silicon chip for use with the present invention will depend on the silicon wafer or semiconductor being processed with the wet chemicals.

The present invention also comprises a sample puck attached to the silicon chip, which serves to hold the silicon chip. The side of the silicon chip opposite the side exposed to the semiconductor processing chemical is coated with a low resistance coating, such as gold, silver, platinum, or copper. Alternatively, a liquid metal such as a Ga/In eutectic may be used to create the electrical contact between the sample puck and the silicon chip. In one embodiment of the present invention, the sample puck is made of stainless steel.

In another embodiment, the apparatus of the present invention is a silicon sensor for detecting impurities in wet chemicals used in semiconductor wafer processing comprising a silicon chip having an electrically connective surface and an operative surface. The operative surface is exposed to the wet chemicals. The operative surface of the silicon chip may also have disposed thereon an oxide layer. A sample puck holds the silicon chip and is electrically connected to the electrically connective surface of the silicon chip. The sample puck is in electrical contact with a pH meter. A reference electrode is also electrically connected to the pH meter. The pH meter is then connected to a recording device which compares the relative outputs of the silicon sensor and the reference electrode to detect impurities in wet chemicals used in semiconductor wafer processing. The recording device for use with the present invention may be a computer, a printer, a cathode ray, or saved to a static or temporary memory. Alternatively, an alarm may be connected directly to the pH meter or to the recording device, which signals that a predetermined level of contamination of the wet chemicals has been reached.

The present invention is also directed to a process for detecting impurities in wet chemicals used for semiconductor wafer processing comprising the steps of measuring the output of a silicon sensor in a reference solution and detecting the output from a reference electrode in the same reference solution. The outputs from the silicon sensor and the reference electrode are compared to obtain a baseline measurement. Next, a sample is obtained and silicon sensor and the reference electrode of the present invention are placed in contact with the sample. By comparing the relative output from the silicon sensor and the reference electrode in the sample to the baseline measurement, the level of contamination in the sample is determined.

In one embodiment, an additional step of recording the baseline and the sample may be recorded using, for example, a computer. Using the present invention, a sample may be measured continuously, by placing the silicon sensor and the reference electrode of the present invention "inline" by integrally attaching them to a reflow tank. Alternatively, the sample may be continuously measured by attaching the silicon sensor and the reference electrode to a wet chemical recirculation line.

BRIEF DESCRIPTION OF THE DRAWINGS

For a more complete understanding of the features and advantages of the present invention, reference is now made to the detailed description of the invention along with the accompanying figures, in which corresponding numerals in the different figures refer to corresponding parts and in which:

FIG. 2 is an enlarged cross-sectional view of a silicon sensor of the present invention;

FIG. 3 is a cross-sectional view of an alternative embodiment of the present invention where the silicon sensor forms an integral part of a semiconductor chemical processing tank;

DETAILED DESCRIPTION OF THE INVENTION

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention.

The present invention is an apparatus and method for monitoring chemical solutions used in the processing of semiconductor silicon wafers, commonly referred to as wet chemicals. More specifically, the present invention is a silicon sensor used to detect impurities and contaminants produced during semiconductor wafer washing and polishing. Using the silicon sensor of the present invention, very low levels of impurities can be detected in chemical solutions that come in contact with silicon wafers during the production of silicon chips. The types of impurities that can be detected using the present invention include both metallic and organic impurities. Examples of metallic impurities may include, for example, Ag, Cu, Au, Pt, and Pd. In fact, the present invention may be used to detect any of the metals in rows IIIA and IIB of the periodic table of elements. Semiconductor processing chemicals containing these impurities lead to increased silicon chip failure rates and decreased yields. The impurities attach to the silicon chips on the silicon wafer during, for example, washing steps. The precise features of the present invention are best explained in association with the drawings.

Figure 1:
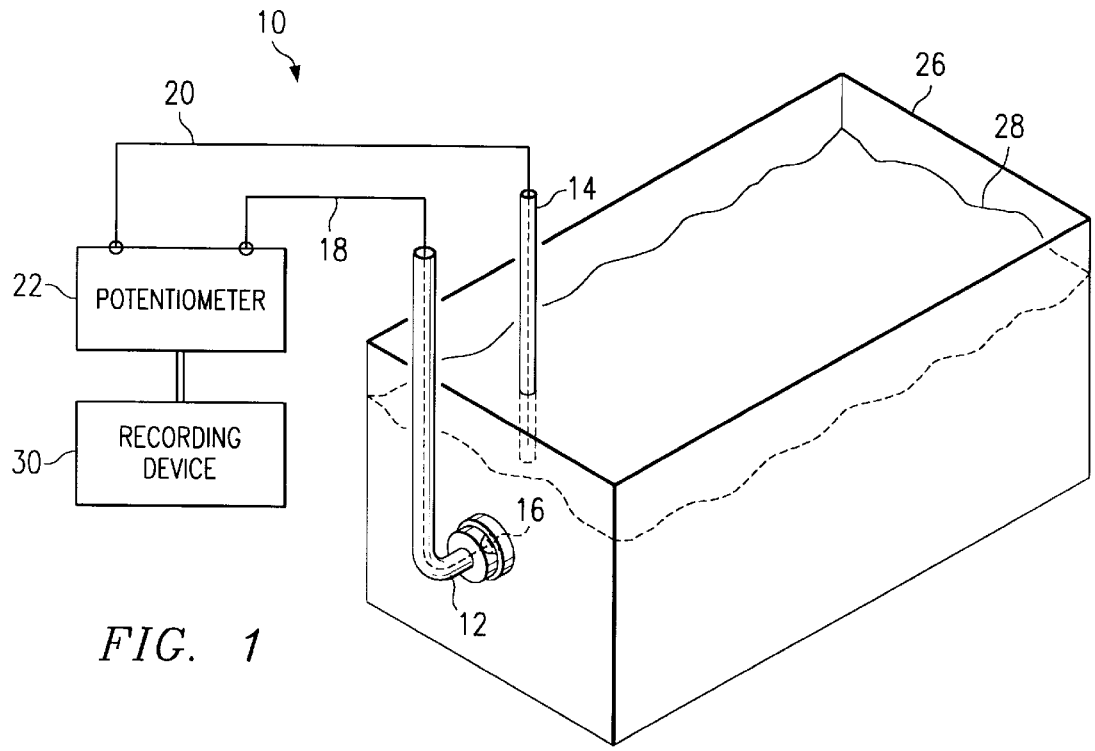
FIG. 1 is a diagram of a silicon sensor located within a semiconductor chemical processing tank.

The general features of the present invention in a semiconductor wafer processing line are shown in FIG. 1 and are generally depicted as 10. A silicon sensor 12 is located within a semiconductor chemical processing tank 26, which contains a semiconductor processing chemical 28. The silicon sensor 12, has a silicon chip 16 in contact with the semiconductor processing chemical 28. The silicon sensor output 18 is carried to a potentiometer 22, which is able to measure an open-circuit potential ($V_{oc}$). Potentiometer 22 may be a pH meter. The potentiometer 22 may be connected to a recording device 30, such as a printer or a computer. A reference electrode 14 is also in contact with the semiconductor processing chemical 28. A reference electrode 14 produces a reference electrode output 20 that is relayed to the potentiometer 22.

A baseline measurement can first be obtained by comparing the silicon sensor output 18 and the reference electrode output 20 at the potentiometer 22 by placing silicon sensor 12 and the reference electrode 14 into a reference solution (not depicted). The reference solution that is used to obtain the baseline measurement will generally be ultrapure semiconductor processing chemical 28 that has not been used in any semiconductor processing steps. Once a baseline measurement has been obtained, the silicon sensor is exposed to the sample to be measured and a comparison between the baseline and the sample measurement is obtained. Using the present invention, sample measurements of contaminants in parts per trillion have been accomplished.

Examples of semiconductor processing chemicals 28 that may be measured include concentrated and dilute: standard clean 1 (SC1), standard clean 2 (SC2), hydrofluoric acid (HF), and deionized water, to name a few. The selection of the solution for measuring the baseline will generally be of the same type of semiconductor processing chemical 28 in the same concentration that is to be measured.

FIG. 2 is a cross-sectional view of the silicon sensor 12 of the present invention. A silicon chip 16 is held in position by a sample puck 38. Disposed between silicon chip 16 and sample puck 38 is a low resistivity coating 36. The low resistivity coating 36 may be a solid metal, such as silver, gold, aluminum, palladium, or copper, for example. Alternatively, the low resistivity coating 36 may be a gallium/indium eutectic.

The sample puck 38 has a conductive pin 40 that provides the electrical connection between the sample puck 38 and a wire 42. The sample puck 38 may be made of, for example, stainless steel. In one embodiment of the present invention, the sample puck 38 has a hollow interior that serves to contain a low resistivity coating 36 that may be liquid, such as a gallium/indium eutectic.

The silicon chip 16 is held in place between the sample puck 38 and an inner O-ring 32. The inner O-ring 32 is, generally, an encapsulated O-ring. In one embodiment, the inner O-ring 32 has a VITON rubber (essentially an inert fluorosilicone material) interior and is coated with polytetrafluoroethylene, sold under the trademark TEFLON ($[CF_2]_n$). Alternatively, the inner o-ring 32 is a Viton rubber O-ring coated with a perfluoroalkoxy polymer.

The inner O-ring 32 is held in place by a sample puck housing 25, depicted here as being threadably and sealably attached to silicon sensor housing 24. While FIG. 2 depicts a threaded connection between sample puck housing 25 and silicon sensor housing 24, the actual manner in which they are connected is relevant only to the extent that a water tight seal is created. The silicon sensor 12 depicted in FIG. 2 is shown with an outer O-ring 34. Outer O-ring 34, like inner O-ring 32, is generally an encapsulated O-ring, which may be, for example, a VITON rubber O-ring coated with a perfluoroalkoxy polymer. While a double O-ring assembly is depicted, the present invention may alternatively include assemblies that prevent fluid leakage, such as, for example, single piece casted single-use silicon sensor 12 assemblies.

The components of the present invention that are in contact with semiconductor processing chemicals 28, other than silicon chip 16, must be chemically resistant and non-contaminating. For example, the silicon sensor housing 24, and the sample puck housing 25 of the present invention may be made of a perfluoroalkoxy polymer. One example of a perfluoroalkoxy polymer that may be used with the present invention is a "Kel-F" perfluoroalkoxy. Alternatively, the entire assembly, except the silicon chip 16, may be coated with a TEFLON-like layer that protects the silicon sensor 12 from semiconductor processing chemical 28.

The silicon chip 16 is positioned with its operative side facing an opening 48. The operative side of the silicon chip 16 of the present invention is the polished side. Alternatively, the silicon chip 16 may have on its operative side an oxide layer. More particularly, the silicon chip 16 selected for the silicon sensor 12 may be the same type as the silicon wafer that is being processed by the semiconductor processing chemicals 28 that are being monitored.

FIG. 2 also shows an opening 48 through which the silicon chip 16 is exposed to semiconductor processing chemicals 28. In one embodiment, the opening 48 is a tapered opening that prevents the formation of an air bubble as the silicon sensor 12 is inserted into a semiconductor chemical processing tank 26. While the sensor depicted in FIG. 2 is shown in a right-angle configuration, other configurations may be used as long as they prevent the formation of air bubbles on the surface of silicon chip 16 that is exposed to the opening 48.

FIG. 3 is a cross-sectional view of an alternative embodiment of the present invention where the silicon sensor 12 forms an integral part of a semiconductor chemical processing tank 26. A silicon chip 16 is held in position by a sample puck 38. The silicon chip 16 has a low resistivity coating 36 that comes in contact with sample puck 38. A conductive pin 40 provides electrical connectivity between sample puck 38 and a wire 42.

The silicon chip 16 is held in place by sample puck 38, inner O-ring 32, silicon sensor housing 24, and sample puck housing 25. As in FIG. 2, the inner O-ring 32 is held in place by a sample puck housing 25, depicted here as being threadably attached to silicon sensor housing 24. The silicon sensor 12 depicted in FIG. 3 is shown with an outer O-ring 34, and a semiconductor processing tank O-ring 46, that prevents the leakage of semiconductor processing chemicals 28 when the silicon sensor 12 is attached to the wall 44 of a semiconductor chemical processing tank 26. Alternatively, the silicon sensor 12 may be attached to part of the semiconductor processing chemical 28 recirculation apparatus (not depicted).

The semiconductor processing tank O-ring 46, like the outer O-ring 34, and inner O-ring 32, is generally an encapsulated O-ring, which may be, for example, a VITON rubber O-ring coated with a perfluoroalkoxy polymer. While a triple O-ring assembly is depicted in FIG. 3, the present invention also includes an assembly that prevents fluid leakage, from the semiconductor chemical processing tank 26, as will be known to those of skill in the art of mechanical attachment.

The silicon sensor housing 24, and the sample puck housing 25 may be made of a perfluoroalkoxy polymer, such as a "Kel-F" perfluoroalkoxy. Alternatively, the entire assembly, except the silicon chip 16, may be coated with a TEFLON-like layer that protects the silicon sensor 12 from a semiconductor processing chemical 28.

The silicon chip 16 is positioned with its operative side facing opening 48, which is a tapered opening that prevents the formation of an air bubble as the silicon sensor 12 comes in contact with a semiconductor processing chemical 28.

Figure 4:
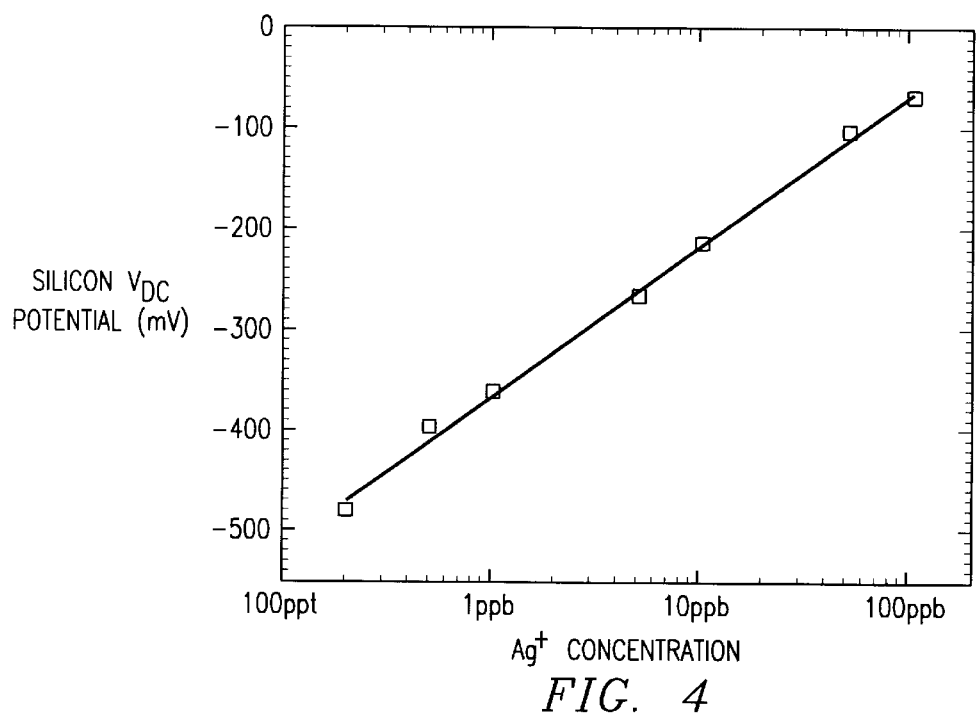
FIG. 4 is a graph showing the sensitivity of the silicon sensor of the present invention.
Figure 5:
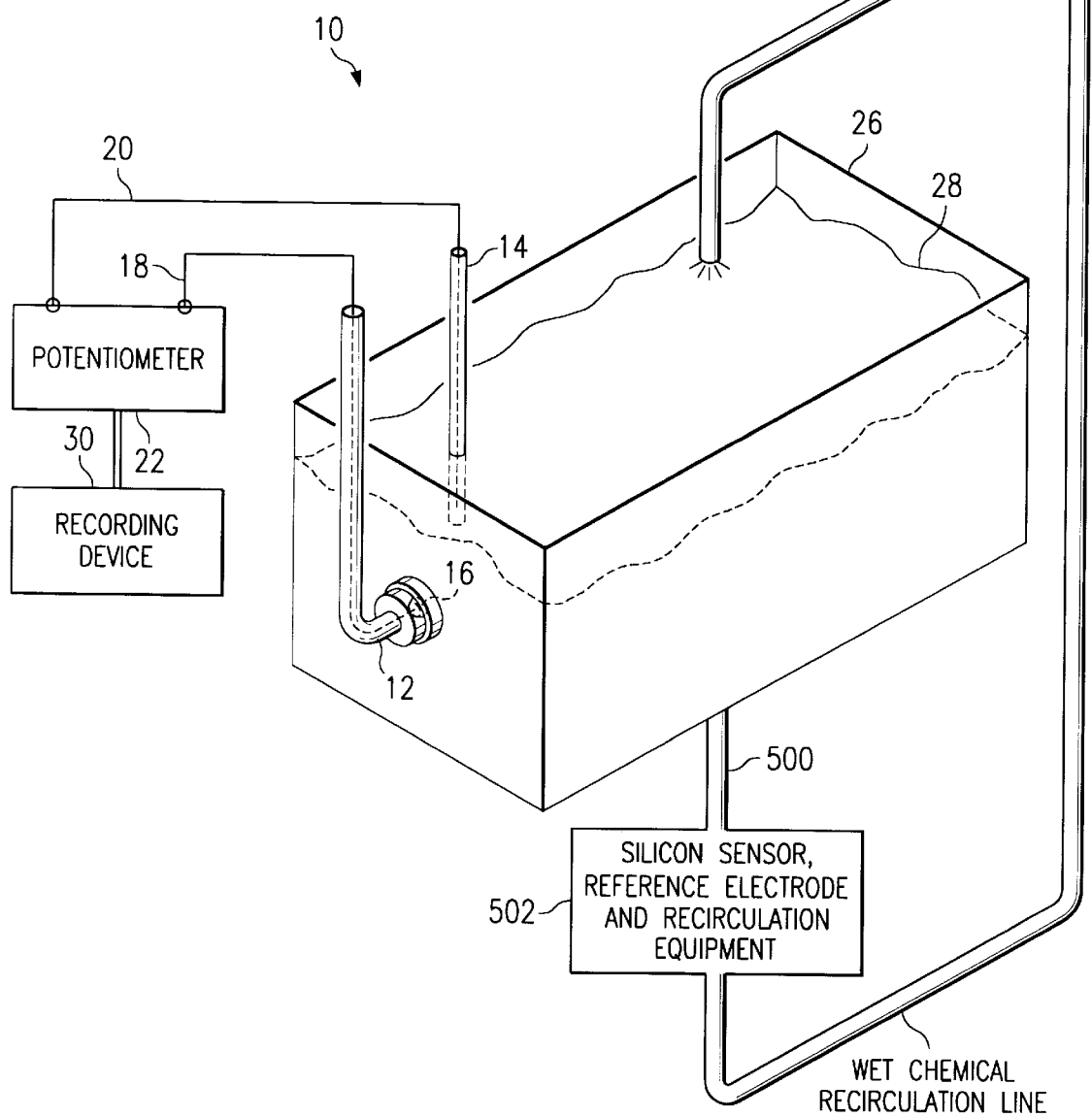
FIG. 5 is a diagram of a silicon sensor located within a semiconductor chemical processing tank and another silicon sensor 502 situated within a set chemical recirculation line 500.

FIG. 4 shows the linear calibration curve of logarithmic concentrations of silver ($Ag^+$) exposed to the silicon sensor 12. $V_{oc}$ potentials were recorded at the end of 90 min detection runs. The detecting sensitivity of the silicon sensor 12 of the present invention toward $Ag^+$ ion in a hydrofluoric acid solution is about 150 mV per decade change of $Ag^+$.

The sensitivity of the silicon sensor 12 of the present invention was found to be more than twice that of an electrochemical sensor that relies solely on the Nernstian equilibrium (59 mV per decade concentration change) at the interface of the sample or semiconductor processing chemical 28 and the operative surface of the silicon chip 16. Atomic force microscopic data (not shown) indicates that the surface of a silicon wafer is rapidly covered by segregated nanometer size metal deposits from outplated metals precipitate from the wash solution. The outplated metal acts to extract surface electrons from the silicon sensor 12 and results in greater positive shift of the open-circuit potential than is expected by the Nerstian equilibrium.

In operation, the present invention may be used to detect impurities in wet chemicals used in semiconductor wafer processing. First, the sensor is washed by boiling the sensor three times in a 10% $HNO_3$, followed by rinsing in ultrapure deionized water (R>18 M Ω). Following the washing steps, the output of the silicon sensor is measured in a ultrapure reference solution, which is the same type of solution that will be sampled. The output from a reference electrode 14, in the same reference solution, is detected and the outputs of the silicon sensor 12 and the reference electrode 14 are compared to obtain a baseline measurement.

Once a baseline measurement has been obtained, the silicon sensor 12 and the reference electrode 14 are then exposed to the sample that is being measured for contamination. Alternatively, the silicon sensor 12 is continuously exposed to a sample, for example, in an inline configuration or in a semiconductor chemical processing tank 26. By contacting the silicon sensor 12 and the reference electrode 14 to the sample, the level of contamination in the sample is determined by comparing the output from silicon sensor 12 and the reference electrode 14 to the baseline measurement to obtain a sample measurement. The comparison between the baseline and the sample may be performed in real-time by attaching the potentiometer 22 that receives the silicon sensor output 18 and the reference electrode output 20 to a recording device 30. The recording device 30 may be, for example, a computer, a cathode ray tube or other display, a printer, or may be saved in permanent or temporary computer memory.

Real time measurements are also achieved by placing the silicon sensor 12 in a semiconductor chemical processing tank 26. Alternatively, like measurements can be made by placing the silicon sensor 12 in an inline configuration. Inline measurements may be obtained by placing the silicon sensor 12 in, for example, a semiconductor processing chemical 28 recirculation line.

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An apparatus for detecting impurities in wet chemicals used in semiconductor wafer processing comprising:

a silicon sensor;

a potentiometer electrically connected to said silicon sensor; and a reference electrode electrically connected to said potentiometer;

wherein said silicon sensor comprises a silicon chip, a low resistivity coating disposed on said silicon chip, and a sample puck that holds said silicon chip and is in electrical contact with said low resistivity coating.

2. The apparatus as recited in claim 1, further comprising:

a housing that isolates the electrical contact between said low resistivity coating and said sample puck from the wet chemicals;

wherein said silicon chip has oppositely disposed polished and unpolished surfaces and said low resistivity coating is disposed on said unpolished surface of said silicon chip.

3. The apparatus as recited in claim 2, wherein said low resistance coating is a Ga/In eutectic.

4. The apparatus as recited in claim 2, wherein said low resistance coating is gold, silver, copper, platinum, or palladium.

5. The apparatus as recited in claim 2, wherein said housing is a fluorinated polymer.

6. The apparatus as recited in claim 2, wherein said housing is coated with polytetrafluoroethylene.

7. The apparatus as recited in claim 2, wherein said silicon chip is a n-Si arsenic-doped chip, a p-type chip, or a polysilicon chip.

8. The apparatus as recited in claim 2, wherein said sample puck is stainless steel.

9. The apparatus as recited in claim 1, further comprising a recording device connected to said potentiometer.

10. The apparatus as recited in claim 1, wherein said reference electrode is a solid state reference electrode, a quasi solid state reference electrode, a double-junction electrode, or a Ag/AgCl double-junction electrode.

11. The apparatus as recited in claim 1, wherein said potentiometer is a pH meter.

12. An apparatus for detecting impurities in wet chemicals used in semiconductor wafer processing comprising:

a silicon chip having an electrically connective surface and an operative surface;

a sample puck for holding said silicon chip, said sample puck electrically contacting said electrically connective surface of said silicon chip;

a potentiometer electrically connected to said sample puck;

a reference electrode electrically connected to said potentiometer; and a recording device connected to said potentiometer for detecting impurities in wet chemicals used in semiconductor wafer processing.

13. The apparatus as recited in claim 12, further comprising a low resistivity coating disposed between said sample puck and said silicon chip.

14. The apparatus as recited in claim 13, wherein said low resistivity coating is further defined as a Ga/In eutectic.

15. The apparatus as recited in claim 12, wherein said potentiometer is a pH meter.

16. The apparatus as recited in claim 12, further comprising an alarm that sounds when impurities in said wet chemicals are detected.

17. A process for detecting impurities in wet chemicals used for semiconductor wafer processing comprising the steps of:

establishing a baseline measurement by comparing the output of a silicon sensor and a reference electrode in a reference solution;

contacting said silicon sensor and said reference electrode with said wet chemicals to obtain a wet chemical measurement;

comparing said wet chemical measurement with said baseline measurement; and determining the level of contamination in said wet chemicals.

18. The process as recited in claim 17, further comprising the step of recording said baseline measurement and said wet chemical measurement.

19. The process as recited in claim 17, further comprising the step of attaching a silicon sensor to a wet chemical reflow tank to continuously contact said silicon sensor and said reference electrode with said wet chemicals.

20. The process as recited in claim 17, further comprising the step of attaching a second silicon sensor to a wet chemical recirculation line to continuously contact said second silicon sensor and said reference electrode with said wet chemicals.

* * * * *